United States Patent [19]
Weidner et al.

[11] Patent Number: 6,056,791
[45] Date of Patent: May 2, 2000

[54] PROCESS FOR THE PRODUCTION OF PARTICLES OR POWDERS

[76] Inventors: Eckhard Weidner, Am Dorfweiher 9, 91056 Erlangen, Germany; Zelijko Knez, Wilsonova 15; Zoran Novak, Askerceva 11, both of 62000 Maribor, Slovenia

[21] Appl. No.: 08/965,805

[22] Filed: Nov. 7, 1997

Related U.S. Application Data

[63] Continuation of application No. 08/694,455, filed as application No. PCT/EP95/00538, Feb. 14, 1995, abandoned.

[30] Foreign Application Priority Data

Feb. 15, 1994 [SI] Slovenia ................................. 9400079

[51] Int. Cl.$^7$ ................................. B01D 9/00; C07C 7/14
[52] U.S. Cl. ..................... 23/295 R; 23/293 R; 23/300; 159/2.1; 203/88; 423/659; 585/812
[58] Field of Search ............................. 23/293 A, 295 R, 23/302 A; 159/2.1; 423/659, DIG. 9, DIG. 11, 625, 629; 585/812; 203/89, 90, 203

[56] References Cited

U.S. PATENT DOCUMENTS

| | | | |
|---|---|---|---|
| Re. 19,456 | 2/1935 | Clayton et al. | 159/2.1 |
| 997,502 | 7/1911 | Kestner | 159/2.1 |
| 1,308,403 | 7/1919 | Doonar | 159/2.1 |
| 1,673,685 | 6/1928 | Johnston et al. | 159/2.1 |
| 3,450,494 | 6/1969 | Gaiser | 159/2.1 |
| 4,906,329 | 3/1990 | Tomiwari et al. | 159/2.1 |
| 5,066,522 | 11/1991 | Cole et al. | 427/422 |

FOREIGN PATENT DOCUMENTS 4-156902  5/1992  Japan ...................................... 159/2.1

*Primary Examiner*—Gary P. Straub
*Attorney, Agent, or Firm*—Wood, Herron & Evans, LLP

[57] ABSTRACT

In a novel process for the production of particles or powders, a substance or mixture of substances to be treated is provided in a pressure vessel. A highly compressible fluid is dissolved under pressure in the substance or mixture of substances provided until a solution containing 5% to 90% by weight of said highly compressible fluid has formed. The melting point of said highly compressible fluid is at least around 40 K lower than the melting point of the substance or mixture of substances to be treated. The solution obtained by dissolving said highly compressible fluid in the substance or mixture of substances provided is adjusted to a temperature of up to around 50 K above or below the melting point under atmospheric pressure of the substance or mixture of substances to be treated and is then rapidly decompressed by means of a decompression device in such a way that the temperature falls, downstream of the decompression device, below the solidification point of the substance or mixture of substances to be treated and essentially all of the highly compressible fluid turns gaseous, whereby particles of the substance or mixture of substances provided form. Subsequently, the particles which have formed are removed from the stream of decompressed highly compressible fluid.

28 Claims, 2 Drawing Sheets

PROCESS FOR THE PRODUCTION OF PARTICLES OR POWDERS

This application is a continuation of applicant's application Ser. No. 08/694,455 filed Aug. 12, 1996, now abandoned, which was a continuation of applicant's parent application number PCT/EP/95/00538, filed Feb. 14, 1995, bearing the same title (in German).

The invention relates to a process for the production of particles or powders.

PRIOR ART

The particles and particle size distributions of solid substances which result in industrial chemical processes are generally not those required or necessary for further use of these substances. Such substances are therefore frequently comminuted or recrystallized. Conventional processes for changing particles sizes and distributions are crushing/grinding, atomization/spray crystallization, freeze drying, sublimation, recrystallization from solutions. The use of said processes is associated with various technical disadvantages. In the mechanical processes there is sometimes considerable heating of the treated substances, which may lead to decomposition of the constituents in the case of thermally unstable substances or mixtures of substances. The thermal processes such as, for example, sublimation or freeze drying can be applied to only a few substances. In crystallization processes solvents are applied commonly which can be removed from the solids only with difficulty and often result as waste.

It is also known to employ highly compressible fluids, for example near-critical or supercritical fluids, for producing particles or powders. Three examples thereof are indicated below:

1. Crystallization From Supercritical Solutions

Compared with conventional solvent crystallization, this process is particularly advantageous when low volatile, thermally sensitive substances are to be crystallized. Fluids with a critical temperature in the region of ambient temperature are employed as non-toxic solvents and as an interesting alternative to classical organic solvents (cf. Tavana A., Randolph A. D., Aiche Journal 1989, 35(10) 1625).

In the conventional cooling crystallization which is carried out batchwise, a saturated solution is cooled, starting from a high temperature at which the solvent has good dissolving capacity, along an optimal cooling curve to the final temperature. The dissolving capacity is thus reduced and the dissolved substance precipitates at least partially. optimization of the cooling curve is necessary in order to adjust to a supersaturation which is as constant as possible and to a constant crystal growth.

In the case where the solvent is a supercritical fluid in which the substance to be crystallized is dissolved, it is likewise necessary to optimize supersaturation and crystal growth. In this case, in distinction from conventional crystallization, the pressure prevailing in the crystallization container is another parameter available for influencing crystal formation. Typical crystallization times are between 30 minutes and several hours. After decompression of the container contents, the crystals are in the form of a solvent-free solid.

2. RESS Process (Rapid Expansion of a Supercritical Solution)

In the RESS process, a solid is dissolved in a supercritical fluid under pressure, and the supercritical solution formed is superheated and is then decompressed to a lower pressure, preferably to atmospheric pressure. Superheating is essential to the RESS process to avoid plugging by premature precipitation of solids in the decompression device. The decompression process reduces the dissolving capacity of the supercritical fluid very rapidly, and the substance to be crystallized precipitates as solid. The applicability of this concept has been shown for some classes of substances. These include polymers (cf. Bush P. J., Pradhan D., Ehrlich P., Macromolecules 1991, 24(6) 1439), dyes (cf. Chang C. J., Randolph A. D., Aiche Journal 1990, 36(6) 939), pharmaceuticals (cf. Tom W. J., Debenedetti P. G., Biotechnol. Prog. 1991, 7, 403) and inorganic substances (cf. Matson D. W., Petersen R. G., Smith R.; Advances in Ceramics 1987, 21, 1090). The supersaturation and the rate of nucleation are influenced by varying the process conditions. It is possible in this way to obtain particles whose size, size distribution and morphology differ very greatly from the solid starting material. It is characteristic of the process that the supersaturation reached, by reason of the cooling and the large reduction in density of the supercritical fluid on decompression, is extremely high.

3. GASR Process (Gas Antisolvent Recrystallization)

This technique is preferably used for substances which are insoluble in supercritical media. In this method, the solubility of a gas under pressure in an organic solvent is utilized in order to reduce the dissolving capacity of this organic solvent for substances dissolved therein. Addition of the gas induces precipitation. It is also possible in this process, by varying the pressure, temperature and type of gas, to vary the properties of the particle populations in wide limits. A considerable advantage of the high-pressure process—the freedom from conventional solvent—is, however, dispensed with in the GASR process.

The known uses of supercritical fluids for producing solids have various disadvantages. The crystallization processes (crystallization from supercritical fluids and gas antisolvent crystallization) can be carried out only batchwise and require long cooling or pressure-changing times (several hours in some cases). After the crystallization phase is complete, the autoclave contents must be decompressed as a whole in order to be able to discharge the solid products. In the case of the GASR process the product results, after the decompression and the removal of gas associated therewith, in suspended form in the solvent or as moist cake of solid. The solid must be removed and dried by suitable measures. Very high pressures and large amounts of gas are necessary for crystallization from supercritical fluids because the relevant substances often have only low solubility in supercritical fluids. Tavana and Randolph (cf. Tavana A., Randolph A. D., Aiche Journal 1989, 35(10) 1625) describe, for example, the crystallization of benzoic acid from a solution in carbon dioxide. Under a pressure of 282.8 bar and at a temperature of 55° C., the solubility of benzoic acid in carbon dioxide is only 2% by weight. Assuming that all the benzoic acid will crystallize, it is accordingly necessary to cool 49 kg of gas to the final crystallization temperature of 35° C. to obtain 1 kg of product. In addition to the thermal energy requirement, considerable amounts of energy are needed for mechanical recompression of the large amounts of gas.

Similar factors also apply to the RESS process. There too, very high pressures of, in some cases, above 600 bar (cf. Matson D. W., Petersen R. G., Smith R.; Advances in Ceramics 1987, 21, 1090) and large excesses of gas are necessary to dissolve solids in the supercritical fluid. Processes requiring several hundred kilograms of gas to obtain 1 kg of powder have been described in the literature.

It is likewise known from gas extraction that supercritical media have a poor dissolving power or capacity for very many substances. Hence very high pressures and large amounts of solvent are necessary both in gas extraction and in the above described processes for producing particles.

SUMMARY OF THE INVENTION

The invention is based on the object of providing a process for producing particles or powders which avoids the abovementioned disadvantages of the classical processes and of the high-pressure processes. In particular, it is an object of the present invention to provide a process for producing particles or powders where the mass ratio between any substance needed to run the process and the actual product is significantly more favorable than with conventional processes. In addition, it is an object of the present invention to provide a process for producing particles or powders from substances which upon heating decompose before they melt.

DESCRIPTION OF THE INVENTION

Figure 1:
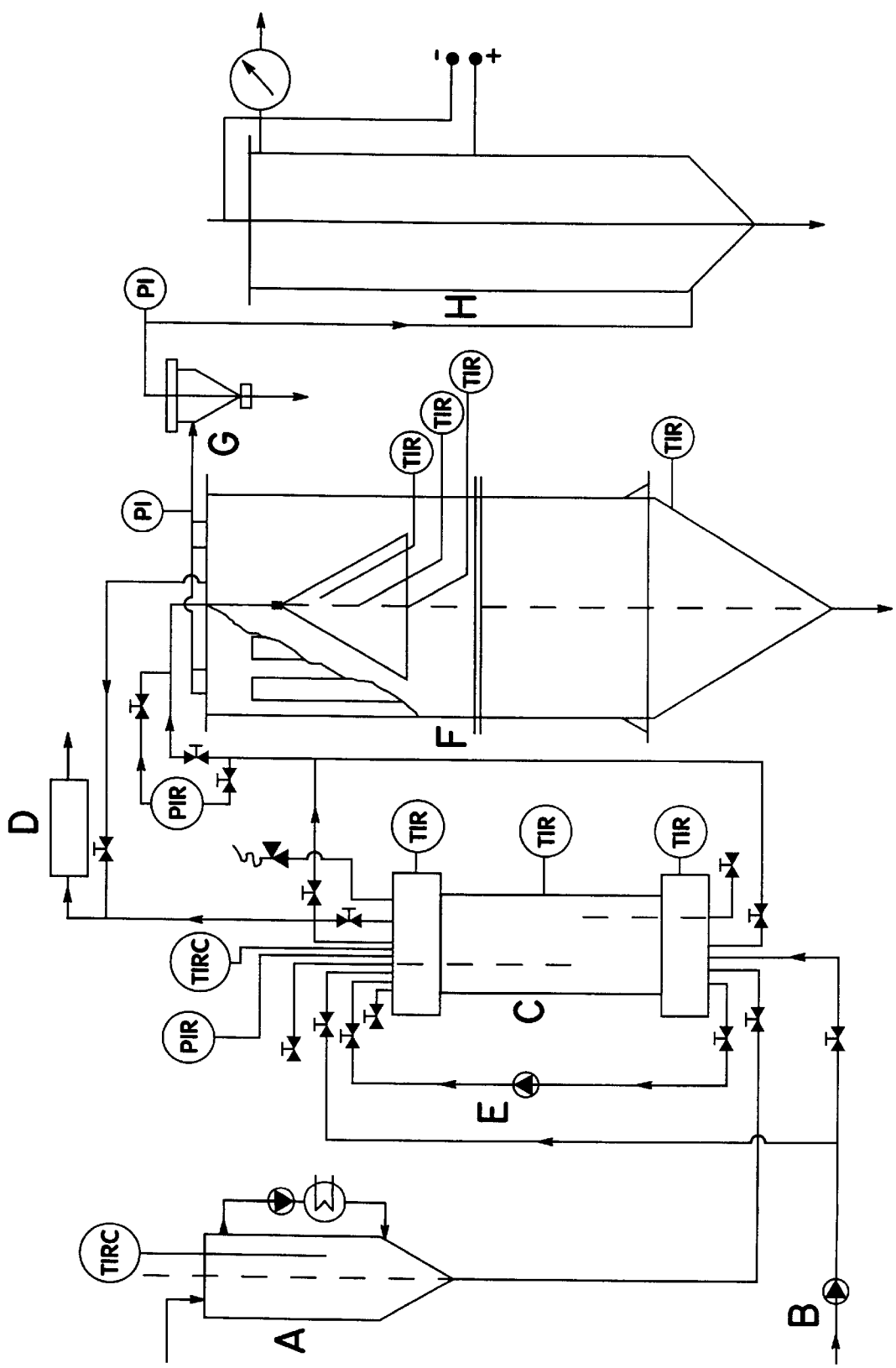
FIG. 1 is a graph showing composition of the coexisting phases in the system Monoglycerides-Carbon Dioxide as a function of pressure and temperature.

The process according to the present invention solves these and other objects. Preferred embodiments and further developments of the process according to the invention are indicated in the dependent claims.

The process according to the invention is based on the surprising finding that it is unnecessary for producing particles from a substance to dissolve this substance in a supercritical gas phase as it is e.g. done in the known RESS process. On the contrary, it is entirely sufficient to dissolve under pressure a gas or, in general, a highly compressible fluid in the substance to be treated. The melting point of said highly compressible fluid should be at least around 40 K lower than the melting point of the substance or mixture of substances to be treated. The solution produced in this way, which solution contains only 5 to 90% by weight of said highly compressible fluid and is preferably saturated with highly compressible fluid, is adjusted to a temperature of up to around 50 K above or below the melting point under atmospheric pressure of the substance or mixture of substances to be treated and is then conveyed to and rapidly decompressed in a suitable decompression device. Conditions are selected such that essentially all of the highly compressible fluid escapes on decompression, i.e. all of or at least essentially all of the highly compressible fluid will turn gaseous on decompression, and brings about a cooling which is so pronounced that the temperature falls below the solidification point of the substance to be treated. The substance precipitates in fine-particle form and is removed from the stream of gas by suitable processes (for example sedimentation, cyclone, filtration, electrofiltration) and, if required, fractionated. Since the procedure is as just described, the process according to the invention is also referred to hereinafter as the PGSS process (Particles from Gas Saturated Solutions).

The term "highly compressible fluid" as used herein is defined by way of the reduced temperature ($T_{reduced}$) and the reduced pressure ($p_{reduced}$) of the substance (in pure form) used as highly compressible fluid. With $$T_{reduced} = \frac{T[K]}{T_{critical}[K]}$$

and $$p_{reduced} = \frac{p[bar]}{p_{critical}[bar]}$$

a fluid is defined in the present application as being highly compressible if its reduced temperature is in a range of 0.5 to 2.0 and its reduced pressure is between 0.3 and 8.0. Preferably, the reduced temperature of the highly compressible fluid is in a range of 0.8 to 1.7. The highly compressible fluid may thus be subcritical with regard to temperature and supercritical with regard to pressure or vice versa or may be subcritical with regard to both temperature and pressure or may be supercritical with regard to both temperature and pressure.

Suitable highly compressible fluids are a whole series of substances. In a preferred embodiment, carbon dioxide, short-chain alkanes, dinitrogen monoxide, nitrogen alone or in mixtures are employed. However, in principle, it is possible to use the vapor phase of any of the substances mentioned in Table 1, and mixtures of these substances, as highly compressible fluid.

TABLE 1

| Compound | Boiling point [°C.] | Critical temperature [°C.] | Critical pressure [bar] | Critical density [kg/m³] |
| --- | --- | --- | --- | --- |
| $CO_2$ | −78.5 | 31.3 | 72.9 | 0.448 |
| $NH_3$ | −33.35 | 132.4 | 112.5 | 0.235 |
| $H_2O$ | 100.00 | 374.15 | 218.3 | 0.315 |
| $N_2O$ | −88.56 | 36.5 | 71.7 | 0.45 |
| $CH_4$ | −164.00 | −82.1 | 45.8 | 0.2 |
| Ethane | −88.63 | 32.28 | 48.1 | 0.203 |
| Ethylene | −103.7 | 9.21 | 49.7 | 0.218 |
| Propane | −42.1 | 96.67 | 41.9 | 0.217 |
| Propylene | −47.4 | 91.9 | 45.4 | |
| n-Butane | −0.5 | 152.0 | 37.5 | |
| i-Butane | −11.7 | 134.7 | 35.9 | |
| n-Pentane | 36.1 | 196.6 | 33.3 | 0.232 |
| Benzene | 80.1 | 288.9 | 48.3 | 0.302 |
| Methanol | 64.7 | 240.5 | 78.9 | 0.272 |
| Ethanol | 78.5 | 243.0 | 63.0 | 0.276 |
| Isopropanol | 82.5 | 235.3 | 47.0 | 0.273 |
| Isobutanol | 108.0 | 275.0 | 42.4 | 0.272 |
| Chlorotrifluoromethane | −31.2 | 28.0 | 38.7 | 0.579 |
| Monofluoromethane | 78.4 | 44.6 | 58.0 | 0.3 |
| Toluene | 110.6 | 320.0 | 40.6 | 0.292 |
| Pyridine | 115.5 | 347.0 | 55.6 | 0.312 |
| Cyclohexane | 80.74 | 280.0 | 40.2 | 0.273 |
| Cyclohexanol | 155.65 | 391.0 | 25.8 | 0.254 |
| o-Xylene | 144.4 | 357.0 | 35.0 | 0.284 |

The substance to be treated can, under ambient conditions, be either a solid or a liquid. If the substance to be treated or the mixture of substances to be treated is in the form of a solid, a liquid solution forms by dissolving under pressure the highly compressible fluid in the solid (provided, of course, that mutual solubility exists). The mass ratio between the highly compressible fluid and the substance to be treated is in this case between 0.1:1 and 4:1 and is thus 2 to 3 orders of magnitude less than in the other high-pressure process techniques for producing solids.

In order to fully understand the present invention it is necessary to appreciate what is meant by dissolving or solubilizing a highly compressible fluid in a liquid or a solid substance. To this end FIG. 1 shows the phase behaviour (coexisting phases) of liquid monoglycerides and carbon dioxide.

FIG. 1 shows pressure versus composition of both the liquid and the gas phase at various temperatures. Graphs on the left give the composition of liquid monoglycerides saturated with carbon dioxide. As can be seen, only a few percent of carbon dioxide dissolve in the liquid monoglycerides when the pressure is low. With increasing pressure, significantly more carbon dioxide dissolves; at a pressure of 100 bar between 11% and 17% by weight of carbon dioxide dissolves in the liquid monoglycerides depending on the prevailing temperature. On the contrary, graphs on the right show that regardless of pressure and temperature almost no (far less than 1% by weight) liquid monoglycerides dissolve in carbon dioxide. This is where conventional processes as e.g. the RESS process operate to obtain the high cooling effect which was heretofore deemed necessary for producing solid particles from liquids.

The solubility of gases in liquids or solids is thus considerably greater than that of liquids or solids in gases. As a further example, the solubility of stearic acid in ethane at a temperature of 80° C. and under a pressure of 37 bar is just 0.002% by weight while the solubility of ethane in stearic acid under the same conditions of pressure and temperature is as much as 5.62% by weight.

The PGSS process of the present invention thus allows to obtain solid particles from liquid solutions having a much higher content of the substance(s) of interest and a far lower gas content than was previously considered necessary. It has been found, surprisingly and unpredictably for even the skilled worker, that the cooling is so great, despite the unusually low gas content and high liquid content, that the temperature falls below the solidification point of the substance to be treated downstream of the decompression device. On decompression of a gas-containing liquid solution of, for example, ethane in stearic acid in a suitable device, e.g. a commercially obtainable high-pressure nozzle, the highly compressed fluid, in this case ethane, is returned to the gaseous state and the substance to be treated precipitates as a fine-particle solid.

For the solidification point to be reached upon decompressing the solution it is necessary to comply with certain outline conditions. One guideline relates to the highly compressible fluid itself: The melting point of the highly compressible fluid used should be at least around 40 K, preferably at least around 80 K, and most preferably at least around 100 K lower than the melting point of the substance or mixture of substances to be treated.

Another guideline relates to the amount of highly compressible fluid contained in the solution: To assure that the cooling effect upon decompressing the solution is pronounced enough for particles to form there has to be a certain minimum amount of highly compressible fluid present in the solution. Depending on the substance or a mixture of substances to be treated and the type of highly compressible fluid used that minimum amount may be between 5% and 90% by weight of highly compressible fluid. Preferably, the minimum amount of highly compressible fluid present in the solution is between 8% and 70% by weight, and most preferably between 10% and 50% by weight.

A further guideline is that the temperature of the solution before decompression should, in the case of a substance or a mixture of substances to be treated which has a clearly defined melting point (under atmospheric pressure), be in the region of up to 50 K, preferably up to 20 K, and most preferably up to 10 K above or below that melting point under atmospheric pressure. The process according to the invention will result in a solution of a substance or of a mixture of substances to be treated even at temperatures below the melting point of this substance or mixture of substances under standard conditions, that is say under atmospheric pressure. It is thus evident that the melting point of a substance or of a mixture of substances to be treated is reduced by dissolving therein under pressure a highly compressible fluid. This is further outlined by way of FIG. 2 which shows the melting point of some organic compounds as a function of gas pressure. Line 1 is Oleic Acid-Carbon Dioxide; line 2 is Glycerol-1-Monooleate-Propane; line 3 is Glycerol-1-Monooleate-Carbon Dioxide; line 4 is Citric Acid-Carbon Dioxide.

Figure 2:
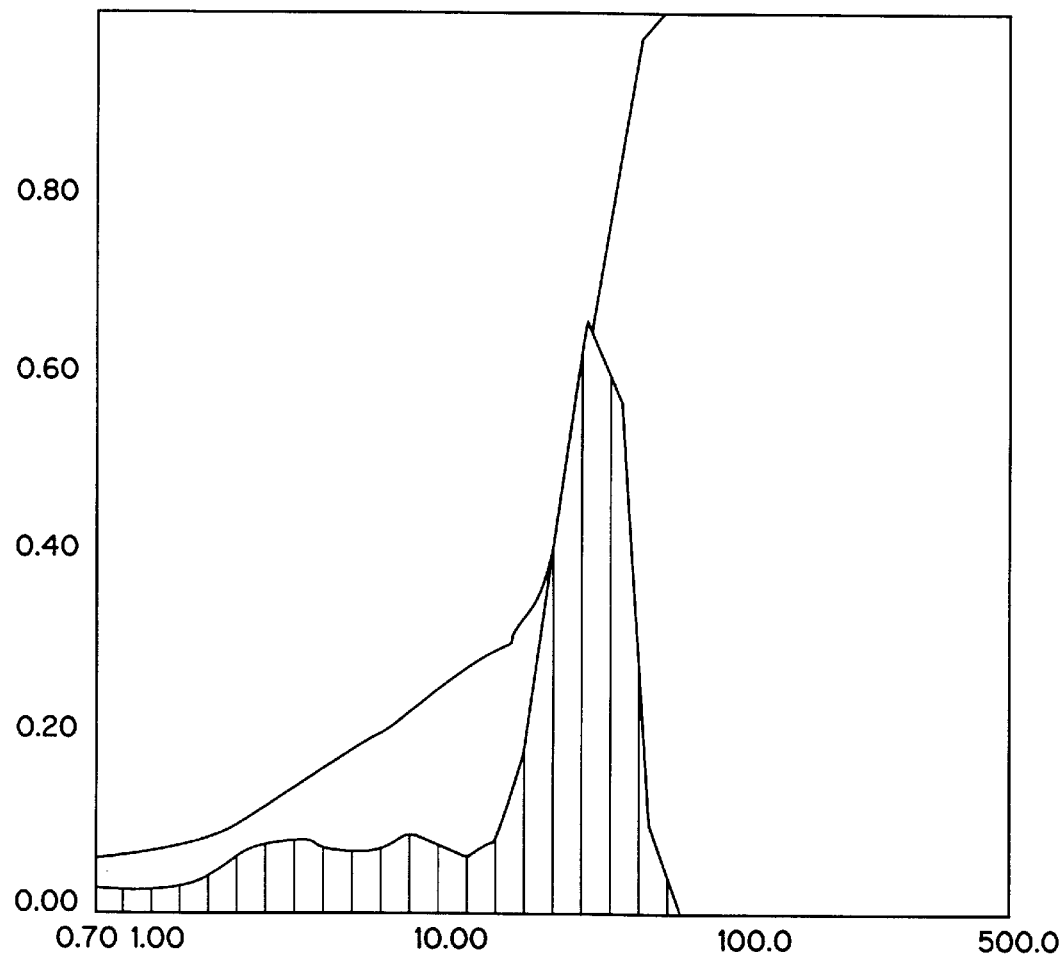
FIG. 2 is a graph showing the melting point of some organic compounds as a function of gas pressure.

FIG. 2 shows the melting point of four binary systems. On the left-hand side of the graphs is the region of solid substance and gaseous highly compressible fluid (carbon dioxide and propane, respectively). On the right-hand side of the graphs is the region of a liquid solution of the substance or mixture of substances to be treated, in this case oleic acid, glycerol-1-monooleate or citric acid, respectively, in equilibrium with the highly compressed fluid. For pure substances, i.e. without a binary component, the pressure dependency of the melting point is usually given by a graph starting at the triple point of the pure substance and having a positive inclination as the pressure increases (water being the notable exception). As can be seen from the diagram, however, if pressure is increased by way of a highly compressible fluid which has a certain solubility in the pure substance under consideration the temperature at which a liquid solution forms decreases. In some cases (cf. systems 1, 2, and 3 above), the temperature at which a liquid solution forms increases with increasing pressure after having passed a slight minimum without, however, reaching the temperature needed to form a liquid solution at ambient pressure.

According to the present invention it is therefore possible to achieve a solution of a substance or of a mixture of substances to be treated even at temperatures below the melting point of this substance or mixture of substances in pure form. Generally and with respect to the above diagram, the present invention seeks to have conditions which are on the right-hand side of the respective graph before decompression and which are on the left-hand side of said graph after decompression in order to obtain a dry pulverous product.

As a further example, it has been found that the melting point of glycerol 1-stearic ester, which is at 75° C. under atmospheric pressure, declines to 58° C. in a carbon dioxide atmosphere of 150 bar. Under a propane atmosphere, a melting point of 58° C. is already reached under a pressure of only 20 bar.

The above is of particular importance in the treatment of substances which decompose even before reaching their (theoretical) melting point. By selecting a suitable highly compressible fluid, it is possible according to the invention to achieve liquid solutions at temperatures which are distinctly below the decomposition point.

In another embodiment of the process according to the invention, the melting point of a substance or mixture of substances to be treated is reduced by adding a solid auxiliary substance which forms a solution with the substance or mixture of substances to be treated. "Solid" here means that the solid auxiliary substance is solid under standard conditions. The solid auxiliary substance is added before or during dissolving of the highly compressible fluid. Preferably, the solid auxiliary substance is chosen such that it forms, with respect to the melting point(s) of the pure components, a low-melting eutectic with the substance or mixture of substances to be treated. A highly compressible fluid is dissolved as described above, in the mixture formed in this way and the resulting liquid solution is rapidly decompressed, again as described before. The mixture solidifies due to the cooling after decompression and solid particles are obtained.

The PGSS process provided according to the present invention is a particularly interesting and universal alternative to conventional processes for producing particles. The main advantages compared with conventional processes are:

considerably lower pressures than in crystallization from supercritical solutions or in the RESS process excellent flexibility and considerably smaller requirement of highly compressible fluid because of the good solubility of the highly compressible fluids in liquids; 0.1–1 kg of highly compressible fluid per kilogram of solid produced is typical, and this value is unusually low by comparison with classical processes for producing solids, for example spray drying, spray crystallization and low-temperature grinding, since gases are required in the form of drying media or as cooling medium in the processes just mentioned. Typical figures for gas consumption are therefore between 2 and 20 kg of gas per kg of solid in those cases.

possibility of circulating the highly compressible fluid after the solids have separated out no waste streams or residual solvents to be disposed of the solid particles produced are free of solvent the PGSS process can be applied successfully to products which cannot be powdered by other processes (for example waxes and resins or else polymeric compounds with unusual rheological properties)

the process is suitable for thermally sensitive substances because low temperatures can be used the process is also suitable for powdering mixtures of substances; the temperature at which the highly compressible fluid dissolves can be widely influenced by suitable selection of solid auxiliary substances dust explosions are avoided when inert gases are used as highly compressible media.

Preferred examples of the process according to the invention are explained in detail hereinafter, also referring to the appended drawings, which show:

FIG. 3 a diagrammatic representation of an apparatus suitable for carrying out the process according to the invention, and FIG. 4 a particle size distribution obtained in one test (see Example 4).

An apparatus suitable for carrying out the process according to the invention is explained in detail by means of FIG. 3. A substance to be treated or a mixture of substances to be treated is melted in a feed vessel 20. An autoclave 24 (V=5 liters, $p_{max}$=400 bar, $T_{max}$=250° C.) is evacuated before starting the test. Subsequently, the molten substance or mixture of substances is sucked in. A highly compressible fluid which is a gas in this case is conveyed into the autoclave 24 up to the required pressure using a high-pressure pump 28 which is operated by compressed air in this case. The pressure is measured by an analog manometer (0–600 bar).

A high-pressure circulating pump 32 is used to draw off the liquid phase at the base of the autoclave and convey it to the top of the autoclave 24. The liquid phase circulation intensifies material exchange between the liquid and gaseous phase; the rate of dissolution of the gas in the liquid is increased. During the dissolution of the gas, the pressure and temperature are manually corrected where appropriate via control loops. The autoclave 24 is provided with sampling devices with whose aid it is possible to measure the gas content in the liquid phase. When the required gas content is reached, the spray process is initiated. To do this, the gas-containing liquid is passed via a thermostated line to the top of a spray tower 36 which has previously been evacuated by means of a vacuum pump and/or flushed with inert gas (for example $CO_2$, $N_2$) in order to preclude the danger of dust explosions with atmospheric oxygen. The gas-containing liquid is decompressed through a suitable decompression device, for example a high-pressure nozzle. It is also possible alternatively to employ other decompression devices (manual valve, control valve, capillaries, orifices etc.). In another embodiment it is possible for an additional gas stream to be metered in directly upstream of the nozzle or in the nozzle. Smaller particle sizes can be obtained in this way.

The mass flow of gas-containing liquid fed to the spray tower 36 can be measured by a mass flow apparatus according to the Coriolis principle. In order to avoid a fall in pressure in the autoclave during the spray process, fresh, preheated gas is metered into the top of the autoclave 24 by the high-pressure pump 28.

On decompression of the solution containing the highly compressed gas, the latter is converted back into the gaseous state. This results in cooling of the mixture of highly compressible fluid and substance or mixture of substances to be powdered, and in precipitation of solid. The temperature and the temperature distribution in the spray tower 36 can be measured with displaceable thermoelements. The spray tower 36 has dimensions such that preferentially particles with an equivalent diameter of 10 $\mu$m are deposited by sedimentation. The particles are collected in a discharge vessel or can be continuously discharged using a suitable apparatus (airlock, screw, fluidized bed with overflow inter alia). The spray tower 36 can be provided with viewing windows to inspect the spray process.

The gas stream from which the larger particles have been removed leaves the spray tower 36 at the upper end and is fed to a cyclone. The cyclone has dimensions such that preferentially particles with a size above 1 $\mu$m are deposited. The particles are collected in a discharge vessel fixed on the lower end of the cyclone.

To remove particles below 1 $\mu$m, the gas stream leaving the cyclone is passed through an electric field in an electrostatic precipitator. The supply voltage is 20 kV. The particles are deposited on a central wire and shaken off at regular intervals. It is also possible, as an alternative to the electrostatic precipitator, to employ other fine filters (for example fabric filters and the like).

The residual gas is passed out of the system through a volume flow gauge and can be recompressed and returned to the autoclave 24. The gas can also, where appropriate, be continuously extracted from the system by means of a blower.

The system and mode of operation described comprise one possible embodiment of the process. Reference has been made to some other embodiments and modifications. Other industrially relevant alternatives comprise in particular the generation of the required solution from highly compressible fluid and substance or mixture of substances to be treated. It is possible in this case to employ, in place of the autoclave 24, for example a static mixer in which the material exchange between liquid and highly compressible fluid is particularly efficient. The process can be operated continuously when a static mixer is used.

EXAMPLES

Example 1

Glyceride mixtures from palm kernel oil which are starting materials for producing emulsifiers and detergents are sprayed using propane. The melting point of the product, which consists of 60% monoglycerides, 37% diglycerides and 2% triglycerides, and 1% free fatty acids, is 44° C. The product is saturated with propane in an autoclave at a temperature of 45° C. and under a pressure of 260 bar and sprayed through a nozzle. The height of free fall after emerging from the nozzle is 0.25 m. A fine-particle powder with an average particle size of 10.5 μm is obtained. The temperature of the powder immediately after spraying is 0° C. The apparent density of the powder is 80 g/l.

Example 2

The mixture from Example 1 forms a liquid solution with propane under a pressure of 230 bar and at a temperature of 37° C. (which is 7° C. below the melting point under atmospheric conditions). The propane-containing (about 35% by weight) glycerides are sprayed through a nozzle. The height of fall after emerging from the nozzle is 1.0 m. The average particle size is 9.5 μm. The temperature after decompression is –3° C. The apparent density of the resulting powder is 55 g/l.

Example 3

Propane is dissolved in the glyceride mixture from Example 1 at a temperature of 47° C. and under a pressure of 20 bar. The propane content is 22% by weight. The liquid solution formed in this way is sprayed through a nozzle. The height of fall after emerging from the nozzle is 1.0 m. The average particle size is 25 μm. The temperature after decompression is 30° C.

Example 4

Monoglycerides of stearic acid are employed on a large scale as physiologically acceptable, highly effective emulsifier in food technology. A glycerol 1-stearic ester with a melting point of 75° C. and a purity of 99% by weight is sprayed. Carbon dioxide is dissolved under a pressure of 80 bar in the monostearate at a temperature of 85° C. The mass ratio between carbon dioxide and monostearate is 0.18:1. After spraying through a nozzle (height of fall about 1.8 m), a fine-particle white powder with an average particle size of 12.8 μm and an apparent density of 39 g/l is obtained. A powder with an average particle size of 7.8 μm is drawn off from the cyclone. A few mg of particles with a particle size <1 μm are deposited in the electrostatic precipitator. The particle size and particle size distribution of the powder drawn off from the spray tower are shown in FIG. 4, and the numerical values are shown in Tab. 2.

Example 5

Citric acid has a melting point of 156° C. under atmospheric pressure. Citric acid is mixed in the mass ratio 1:3 with polyethylene glycol having an average molecular weight of 1500 g/mol and a melting range of 44–48° C. The mixture produced in this way melts in a temperature range between +2 and +5° C., that is to say the two substances form a eutectic with a melting point below the melting points of the two pure substances. Carbon dioxide is dissolved under a pressure of 200 bar in the mixture of citric acid and polyethylene glycol in a pressure vessel at a temperature of 20° C. The gas-containing solution formed in this way is decompressed in a nozzle. A coprecipitate of citric acid and polyethylene glycol in powder form with a temperature of –5° C. results. The average particle size is 300 μm. It is accordingly possible, by adding a suitable auxiliary, to reduce the temperature at which the required product (in this case citric acid) is to be saturated with gas considerably below the melting point of the product under atmospheric conditions.

Example 6

Carbon dioxide is dissolved under a pressure of 200 bar in a polyether with an average molecular weight of 3500 g/mol and a melting point of 42° C. at a temperature of 45° C. The gas-containing solution is decompressed through a manually operated metering valve into a collecting vessel. The height of the fall to the bottom of the collecting vessel is about 0.4 m. A powder with a wide particle size distribution between 200 μm and 2000 μm is obtained. The fraction above 1 mm was screened off and returned to the process.

Example 7

A pharmaceutical agent (dimethyl 1,4-dihydro-2,6-dimethyl-4-(2-nitrophenyl)-3,5-pyridinedicarboxylate, trivial name: nifedipine) was treated by the PGSS process. Carbon dioxide was dissolved in the product at a temperature of 170° C. and under a pressure of 200 bar. A powder with an average particle size of 10 μm was obtained by spraying through a nozzle. The mass ratio of gas to solid is 0.1:1.

Example 8

Carbon dioxide is dissolved under a pressure of 80 bar in glycerol 1-stearic ester at a temperature of 85° C. The mass ratio between carbon dioxide and monostearate is 0.18:1. Immediately before spraying through a nozzle, nitrogen is metered into the gas-containing liquid. The ratio of the mass flows of nitrogen to gas-containing liquid is 0.5:1. After decompression in the nozzle (height of fall about 1.8 m), a fine-particle white powder with an average particle size of 8.2 μm is obtained. This example essentially corresponds to Example 4. However, finer particles are obtained by metering in the additional nitrogen gas stream.

TABLE 2

| Diameter μm | 0.7 | 0.9 | 1.0 | 1.4 | 1.7 | 2.0 | 2.6 | 3.2 | 4.0 | 5.0 |
|---|---|---|---|---|---|---|---|---|---|---|
| Total % contents by mass | 5.2 | 5.9 | 6.2 | 7.5 | 8.7 | 10.2 | 13.0 | 15.4 | 17.8 | 20.1 |
| Diameter μm | 6.0 | 8.0 | 10.0 | 12.0 | 15.0 | 18.0 | 23.0 | 30.0 | 36.0 | 45.0 |
| Total % contents by mass | 22.2 | 26.0 | 28.1 | 30.3 | 36.5 | 48.2 | 73.4 | 97.1 | 100 | 100 |
| Diameter μm | 56.0 | 70.0 | 90.0 | 110 | 135 | 165 | 210 | 260 | 320 | 400 |
| Total % contents by mass | 100 | 100 | 100 | 100 | 100 | 100 | 100 | 100 | 100 | 100 |

We claim:

1. A process for the production of dry particles or powders, comprising the steps of:
   (a) providing in a pressure vessel a non-gaseous substance or mixture of substances to be treated,
   (b) adjusting a temperature of the substance or mixture of substances to a range between about 50° K above or below the melting point under atmospheric pressure and below a decomposition temperature of the substance or mixture of substances,
   (c) selecting a highly compressible fluid having a melting point of at least about 40° K lower than the melting point of the substance or mixture of substances, the selected fluid being highly compressible under conditions of $0.5.T_{critical}$ to $2.0.T_{critical}$ and $0.3.P_{critical}$ to $8.0.P_{critical}$ with regard to said highly compressible fluid,
   (d) pressurizing the substance or mixture of substances provided in the pressure vessel at the temperature in (b) by introducing said highly compressible fluid under conditions of $0.5.T_{critical}$ to $2.0.T_{critical}$ and $0.3.P_{critical}$ to $8.0.P_{critical}$ with regard to said highly compressible fluid until a liquid solution has formed containing 10–95% of the substance or mixture of substances,
   (e) conveying to and passing the solution through a decompression device for rapid decompression, wherein conditions are selected such that the temperature falls, downstream of the decompression device, below the solidification point of the substance or mixture of substances and essentially all of the highly compressible fluid turns gaseous and dry particles of the substance or mixture of substances form, and
   (f) removing from the stream of decompressed highly compressible fluid the dry particles which have formed.

2. The process of claim 1, wherein the solution obtained by dissolving said highly compressible fluid in the substance or mixture of substances provided contains 30 to 92% by weight of said substance or mixture of substances.

3. The process of claim 1, wherein the solution obtained by dissolving said highly compressible fluid in the substance or mixture of substances provided contains 50 to 90% by weight of said substance or mixture of substances.

4. The process of claim 1, wherein the melting point of said highly compressible fluid is at least around 80 K lower than the melting point of the substance or mixture of substances to be treated.

5. The process of claim 1, wherein the melting point of said highly compressible fluid is at least around 100 K lower than the melting point of the substance or mixture of substances to be treated.

6. The process of claim 1, wherein the solution obtained by dissolving said highly compressible fluid in the substance or mixture of substances provided is adjusted to a temperature of up to around 20 K above or below the melting point under atmospheric pressure of the substance or mixture of substances to be treated.

7. The process of claim 1, wherein the solution obtained by dissolving said highly compressible fluid in the substance or mixture of substances provided is adjusted to a temperature of up to around 10 K above or below the melting point under atmospheric pressure of the substance or mixture of substances to be treated.

8. The process of claim 1, wherein the solution obtained by dissolving said highly compressible fluid in the substance or mixture of substances provided is adjusted, if the substance or mixture of substances decomposes on heating under atmospheric pressure before it melts, to a temperature which is below the decomposition temperature under atmospheric pressure of the substance or mixture of substances to be treated and the highly compressible fluid is selected to achieve the solution at said adjusted temperature.

9. The process of claim 1, wherein the pressure during dissolving said highly compressible fluid in the substance or mixture of substances is in the range from 5 to 500 bar.

10. The process of claim 1, wherein the pressure during dissolving said highly compressible fluid in the substance or mixture of substances is in the range from 10 to 200 bar.

11. The process of claim 1, wherein the solution of said highly compressible fluid and the substance or mixture of substances is established in a range of $0.5.T_{critical}$ to $2.0.T_{critical}$ and $0.3.p_{critical}$ and $8.0.p_{critical}$ with regard to said highly compressible fluid.

12. The process of claim 1, wherein the solution of said highly compressible fluid and the substance or mixture of substances is established in a range of $0.8.T_{critical}$ to $1.7.T_{critical}$ and $0.3.p_{critical}$ and $8.0.p_{critical}$ with regard to said highly compressible fluid.

13. The process of any of the preceding claims, wherein the melting point of the substance or mixture of substances to be treated is reduced by means of a solid auxiliary substance, which forms a solution with the substance or mixture of substances to be treated and which is added before or during dissolving of the highly compressible fluid.

14. The process of claim 13, wherein the solid auxiliary substance forms, with regard to the melting point(s) of the substance or mixture of substances to be treated, a eutectic with the substance or mixture of substances to be treated.

15. The process of claim 1, wherein the highly compressible fluid is selected from the group consisting of hydrocarbons with 1 to 6 carbon atoms, alcohols with 1 to 4 carbon atoms, and mixtures thereof.

16. The process of claim 1, wherein the particles which are formed are removed in fractions.

17. The process of claim 16, wherein the particle stream is passed, for the fractional removal, first through a spray tower, then through a cyclone and finally through a fine filter.

18. The process of claim 17, wherein the fine filter is an electrostatic precipitator.

19. The process of claim 1, wherein the solution obtained by dissolving said highly compressible fluid in the substance or mixture of substances provided is decompressed through at least one of the following: a nozzle, a valve, a diffuser and a capillary.

20. The process of claim 1, wherein the highly compressible fluid is selected from the group consisting of carbon dioxide, nitrogen, freons and combinations thereof.

21. The process of claim 1, wherein the highly compressible fluid is selected from the group consisting of a gaseous oxide, an inert gas and combinations thereof.

22. The process of claim 1, wherein the highly compressible fluid is a halogenated hydrocarbon.

23. The process of claim 1, further comprising prior to step (a)
   selecting a highly compressible fluid having a known $T_{critical}$, $P_{critical}$ and melting point,
   selecting a substance or mixture of substances to be treated having a known melting point, and
   determining whether said highly compressible fluid and said substance will fulfill steps (c) and (d).

24. The process of claim 1 wherein the dry particles or powders are in crystalline form.

25. A process for the production of dry particles or powders, comprising the steps of:

(a) pressurizing a pressure vessel by introducing a selected highly compressible fluid into said vessel, said highly compressible fluid having a melting point of at least about 40° K lower than the melting point of a non-gaseous substance or mixture of substances to be treated, the fluid being such that it is highly compressible under conditions of $0.5.T_{critical}$ to $2.0.T_{critical}$ and $0.3.P_{critical}$ to $8.0.P_{critical}$ with regard to said highly compressible fluid, (b) providing to said pressurized vessel said substance or mixture of substances, (c) adjusting a temperature of the substance or mixture of substances to a range between about 50° K above or below the melting point under atmospheric pressure and below a decomposition temperature of the substance or mixture of substances, (d) pressurizing the substance or mixture of substances provided in the pressure vessel at the temperature in (c) with said highly compressible fluid under conditions of $0.5.T_{critical}$ to $2.0.T_{critical}$ and $0.3.P_{critical}$ to $8.0.P_{critical}$ with regard to said highly compressible fluid until a liquid solution has formed containing 10–95% of the substance or mixture of substances, (e) conveying to and passing the solution through a decompression device for rapid decompression, wherein conditions are selected such that the temperature falls, downstream of the decompression device, below the solidification point of the substance or mixture of substances and essentially all of the highly compressible fluid turns gaseous and dry particles of the substance or mixture of substances form, and (f) removing from the stream of decompressed highly compressible fluid the dry particles which have formed.

26. The process of claim 25 wherein the dry particles or powders are in crystalline form.

27. A process for the production of dry particles or powders, comprising:

pressurizing, in a pressure vessel, a non-gaseous substance or mixture of substances, at a temperature adjusted to a range between about 50° K above or below the melting point under atmospheric pressure and below a decomposition temperature of the substance or mixture of substances, with a highly compressible fluid having a melting point of at least about 40° K lower than the melting point of the substance or mixture of substances, the selected fluid being highly compressible under conditions of $0.5.T_{critical}$ to $2.0.T_{critical}$ and $0.3.P_{critical}$ to $8.0.P_{critical}$ with regard to said highly compressible fluid, said pressurizing occurring under conditions of $0.5.T_{critical}$ to $2.0.T_{critical}$ and $0.3.P_{critical}$ to $8.0.P_{critical}$ with regard to said highly compressible fluid, until a liquid solution has formed containing 10–95% of the substance or mixture of substances, thereafter, conveying to and passing the solution through a decompression device for rapid decompression, wherein conditions are selected such that the temperature falls, downstream of the decompression device, below the solidification point of the substance or mixture of substances and essentially all of the highly compressible fluid turns gaseous and dry particles of the substance or mixture of substances provided form, and removing from the stream of decompressed highly compressible fluid the dry particles which have formed.

28. The process of claim 27 wherein the dry particles or powders are in crystalline form.

* * * * *

UNITED STATES PATENT AND TRADEMARK OFFICE
CERTIFICATE OF CORRECTION

PATENT NO. : 6,056,791
DATED : May 2, 2000
INVENTOR(S) : Weidner et al.

It is certified that error appears in the above-identified patent and that said Letters Patent is hereby corrected as shown below:

Title page,
Item [75], Inventors, "Zelijko Knez," should be -- Zeljko Knez --.

Column 1,
Line 49, change "optimization of …" to -- Optimization of … --

Column 9,
Line 34, change "…highly effective emulsifier in food…" to -- ..highly effective emulsifiers in food --

Column 11,
Line 15, change "…$0.5 \cdot T_{critical}$ to $2.0 \cdot T_{critical}$ to $0.3 \cdot T_{critical}$ to $8.0 \cdot P_{critical}$…" to -- $0.5 \cdot T_{critical}$ to $2.0 \cdot T_{critical}$ to $0.3 \cdot T_{critical}$ to $8.0 \cdot P_{critical}$ …--

Column 12,
Line 15, change "…$0.5 \cdot T_{critical}$ to $2.0 \cdot T_{critical}$ to $0.3 \cdot T_{critical}$ to $8.0 \cdot P_{critical}$…" to -- $0.5 \cdot T_{critical}$ to $2.0 \cdot T_{critical}$ to $0.3 \cdot T_{critical}$ to $8.0 \cdot P_{critical}$ …--

Lines 19-20, change "…$0.8 \cdot T_{critical}$ to $1.7 \cdot T_{critical}$ and $0.3 \cdot P_{critical}$ to $8.0 \cdot P_{critical}$" to $0.8 \cdot T_{critical}$ to $1.7 \cdot T_{critical}$ to $0.3 \cdot P_{critical}$ to $8.0 \cdot P_{critical}$ --

Line 21, change "…any of the preceding claims,…" to -- …claim 1,… --.

Column 13,
Lines 7 and 20, change "…$0.5 \cdot T_{critical}$ to $2.0 \cdot T_{critical}$ to $0.3 \cdot T_{critical}$ to $8.0 \cdot P_{critical}$…" to -- $0.5 \cdot T_{critical}$ to $2.0 \cdot T_{critical}$ to $0.3 \cdot T_{critical}$ to $8.0 \cdot P_{critical}$ …--

UNITED STATES PATENT AND TRADEMARK OFFICE
CERTIFICATE OF CORRECTION

PATENT NO. : 6,056,791
DATED : May 2, 2000
INVENTOR(S) : Weidner et al.

It is certified that error appears in the above-identified patent and that said Letters Patent is hereby corrected as shown below:

<u>Column 14,</u>
Lines 14 and 17, change "...$0.5.T_{critical}$ to $2.0.T_{critical}$ to $0.3.T_{critical}$ to $8.0.P_{critical}$..." to -- $0.5 \cdot T_{critical}$ to $2.0 \cdot T_{critical}$ to $0.3 \cdot T_{critical}$ to $8.0 \cdot P_{critical}$ ...--

Signed and Sealed this

Twenty-eighth Day of September, 2004

JON W. DUDAS
*Director of the United States Patent and Trademark Office*